US011033335B2

(12) United States Patent
Zhang (10) Patent No.: US 11,033,335 B2
(45) Date of Patent: Jun. 15, 2021

(54) PLACEMENT OF ORTHOPAEDIC IMPLANT FIXATION APPARATUS

(71) Applicant: Formus Labs Limited, Auckland (NZ)

(72) Inventor: Ju Zhang, Auckland (NZ)

(73) Assignee: FORMUS LABS LIMITED, Auckland (NZ)

( * ) Notice: Subject to any disclaimer, the term of this patent is extended or adjusted under 35 U.S.C. 154(b) by 211 days.

(21) Appl. No.: 16/219,172

(22) Filed: Dec. 13, 2018

(65) Prior Publication Data

US 2019/0175278 A1 Jun. 13, 2019

(30) Foreign Application Priority Data

Dec. 13, 2017 (NZ) ........................................ 738322

(51) Int. Cl.
| | |
|---|---|
| *A61B 34/10* | (2016.01) |
| *A61B 5/00* | (2006.01) |
| *G16H 50/50* | (2018.01) |
| *A61F 2/34* | (2006.01) |
| *G06N 20/00* | (2019.01) |
| *A61B 17/80* | (2006.01) |

(52) U.S. Cl.
CPC ............ *A61B 34/10* (2016.02); *A61B 5/4509* (2013.01); *A61F 2/34* (2013.01); *G16H 50/50* (2018.01); *A61B 17/80* (2013.01); *A61B 2034/105* (2016.02); *A61B 2034/107* (2016.02); *A61B 2576/02* (2013.01); *G06N 20/00* (2019.01)

(58) Field of Classification Search
CPC .............. A61B 34/10; A61B 2034/101; A61B 2034/105; A61B 2034/107; A61B 5/4509; G16H 50/50
See application file for complete search history.

(56) References Cited

U.S. PATENT DOCUMENTS

| | | | |
|---|---|---|---|
| 6,249,692 B1 * | 6/2001 | Cowin ................... | A61B 5/103 324/309 |
| 9,603,670 B2 * | 3/2017 | Brianza .................. | A61B 34/10 |
| 9,937,011 B2 * | 4/2018 | Yosibash ................ | A61B 5/055 |
| 10,166,109 B2 * | 1/2019 | Ferko ..................... | A61B 17/17 |
| 10,226,210 B2 * | 3/2019 | Arad (Abboud) ... | A61B 5/4509 |
| 2004/0009459 A1 * | 1/2004 | Anderson ............... | G06T 19/00 434/262 |
| 2012/0323282 A1 * | 12/2012 | Brianza .................. | A61B 34/10 606/286 |
| 2015/0080717 A1 * | 3/2015 | Ferko ..................... | G06F 30/20 600/425 |
| 2015/0119987 A1 * | 4/2015 | Davignon .............. | G16H 50/50 623/16.11 |

(Continued)

*Primary Examiner* — Eric S Gibson
(74) *Attorney, Agent, or Firm* — Fenwick & West LLP (57) ABSTRACT

The present invention relates to orthopaedic implants and has particular relevance to determining the placement of fixation apparatus or devices, such as screws, which are used to fix implants to the bone or bones with which the implants are to be connected. More particularly, the invention relates to a method for determining placement of a fixation apparatus for fixing an orthopaedic implant to bone, and the method comprising: selecting a plurality of fixation locations; using a bone density model to determine bone density associated with each location; and selecting a combination or permutation of the fixation locations dependent on the determined bone density.

21 Claims, 6 Drawing Sheets

(56) References Cited

U.S. PATENT DOCUMENTS

| | | | |
|---|---|---|---|
| 2016/0100791 A1* | 4/2016 | Arad (Abboud) | A61B 5/6831 |
| | | | 600/547 |
| 2016/0235381 A1* | 8/2016 | Scanlan | A61B 6/032 |
| 2016/0242852 A1* | 8/2016 | Yosibash | G16H 50/50 |
| 2018/0289423 A1* | 10/2018 | Singh | A61B 34/10 |
| 2018/0338839 A1* | 11/2018 | Ferko | A61B 5/4528 |
| 2019/0038213 A1* | 2/2019 | Arad (Abboud) | A61B 5/0536 |
| 2019/0175278 A1* | 6/2019 | Zhang | G16H 20/40 |
| 2020/0129213 A1* | 4/2020 | Singh | A61B 17/1728 |
| 2020/0205898 A1* | 7/2020 | Hampp | A61B 34/10 |
| 2020/0253666 A1* | 8/2020 | Spaelter | A61B 17/1703 |
| 2020/0275880 A1* | 9/2020 | Kopperdahl | A61B 5/055 |

* cited by examiner

PLACEMENT OF ORTHOPAEDIC IMPLANT FIXATION APPARATUS

CROSS-REFERENCE TO RELATED APPLICATION

This application claims priority under 35 U.S.C. 119(a) to New Zealand provisional patent application no. 738322 filed on Dec. 13, 2017, which is incorporate by reference herein in its entirety.

FIELD OF THE INVENTION

This invention relates to orthopaedic implants. The invention has particular relevance to determining the placement of fixation apparatus or devices, such as screws, which are used to fix implants to the bone or bones with which the implants are to be connected.

BACKGROUND

Effective fixation of an orthopaedic implant to the adjacent bone is vital for achieving long term implant stability and performance. A wide range of orthopaedic implants are fixed to patient bones using screws. To create an effective fixation, the position and orientation of a screw should be such that the screw is disposed in strong bone stock. Although this document refers extensively to the use of screws, it should be appreciated that equivalent fixing apparatus or mechanisms, such as nails, pins or rods for example, could be used.

Achieving screw placement in strong bone stock is subject to determining the location of such stock, but it is also subject to a number of other constraints, some of which are explained below.

Firstly, there are practical surgical constraints. These include the positions and orientations for screw placement that are possible to achieve during the required surgical procedure. For example, in practice there are screw placement vectors which cannot be realised because there is no access for surgical instruments.

Secondly, there are anatomical constraints. For example, the screw placement should not damage other adjacent tissue such as muscles or other organs.

Thirdly, there are the constraints imposed by the implant device itself. These constraints differ from one device to another, and are determined by the basic geometry of the device, particularly the available locations that the device provides for screw insertion i.e. the location of screw holes, or places where such holes may be formed.

Although there are known tools available for determining implant design, such as the system disclosed in US patent publication US2015/0119987, these do not assist the surgeon in determining optimum screw placement given constraints such as those outlined above. Therefore, under current procedures, surgery is planned by surgeons and engineers using their know-how to decide where screws should best be placed. This entails a time consuming and highly subjective process, and can result in inconsistent fixation.

SUMMARY OF THE INVENTION

It is an object of the present invention to provide a system or method or apparatus which will at least go some way toward addressing the problems mention above.

Alternatively it is an object of the invention to provide a useful alternative to existing methods, systems or apparatus.

Further objects of the invention will become apparent from the following description.

In one aspect the invention broadly provides a method for determining placement of a fixation apparatus for fixing an orthopaedic implant to bone, the method comprising: selecting a plurality of fixation vectors;

using a bone density model to determine bone density associated with each vector; selecting at least one of the fixation vectors dependent on the determined bone density.

The bone density associated with each vector may be the density along the vector. The density along the vector may be determined by summing or integrating bone density along the vector.

The vector may be extended or reduced dependent on the determined bone density.

A fixation location may firstly be selected for the fixation vectors. Bone density associated with a location may be used to determine whether to select a location.

A plurality of locations may be selected. A plurality of vectors may then be selected for each location.

Vectors may be ranked according to the associated bone density. A selection of vectors with the highest bone density ranking can be determined for each location.

Permutations of the ranked vectors and locations can be generated. A ranking or score can then be determined for each permutation. The permutation with the most favourable ranking may then be selected.

In another aspect the invention broadly provides a method for determining placement of a fixation apparatus for fixing an orthopaedic implant to bone, the method comprising:

selecting a plurality of fixation locations;

using a bone density model to determine bone density associated with each location;

selecting a combination or permutation of the fixation locations dependent on the determined bone density.

A plurality of vectors may be selected for each location.

Vectors may be ranked according to the associated bone density. A selection of vectors with the highest bone density ranking can be determined for each location.

Permutations of the ranked vectors and locations can be generated. A ranking or score can then be determined for each permutation. The permutation with the most favourable ranking may then be selected.

In one aspect the invention broadly provides a method for determining placement of a plurality of fixation apparatus for fixing an orthopaedic implant to bone, the method comprising:

selecting a plurality of fixation locations;

selecting a plurality of fixation vectors for each location;

determining permutations of fixation vectors across the selected fixation locations;

determining a score for each permutation, and;

selecting the permutation with the best score.

The score may be dependent on bone strength. Bone strength may be indicated by bone density.

The score may be dependent on one or more of:

Relative vector proximity;

Relative vector alignment;

The fixation vectors and/or the fixation locations may be selected dependent on bone density.

In another aspect the invention broadly provides a system or apparatus to implement a method or methods disclosed earlier in this section.

The disclosed subject matter also provides an implant fixation placement system and a method which may broadly be said to consist in the parts, elements and features referred to or indicated in this specification, individually or collectively, in any or all combinations of two or more of those parts, elements or features. Where specific integers are mentioned in this specification which have known equivalents in the art to which the invention relates, such known equivalents are deemed to be incorporated in the specification.

Further aspects of the invention, which should be considered in all its novel aspects, will become apparent from the following description.

BRIEF DESCRIPTION OF THE DRAWINGS

One or more examples of the invention are described below with reference to the accompanying drawings, in which.

DETAILED DESCRIPTION

Figure 1:
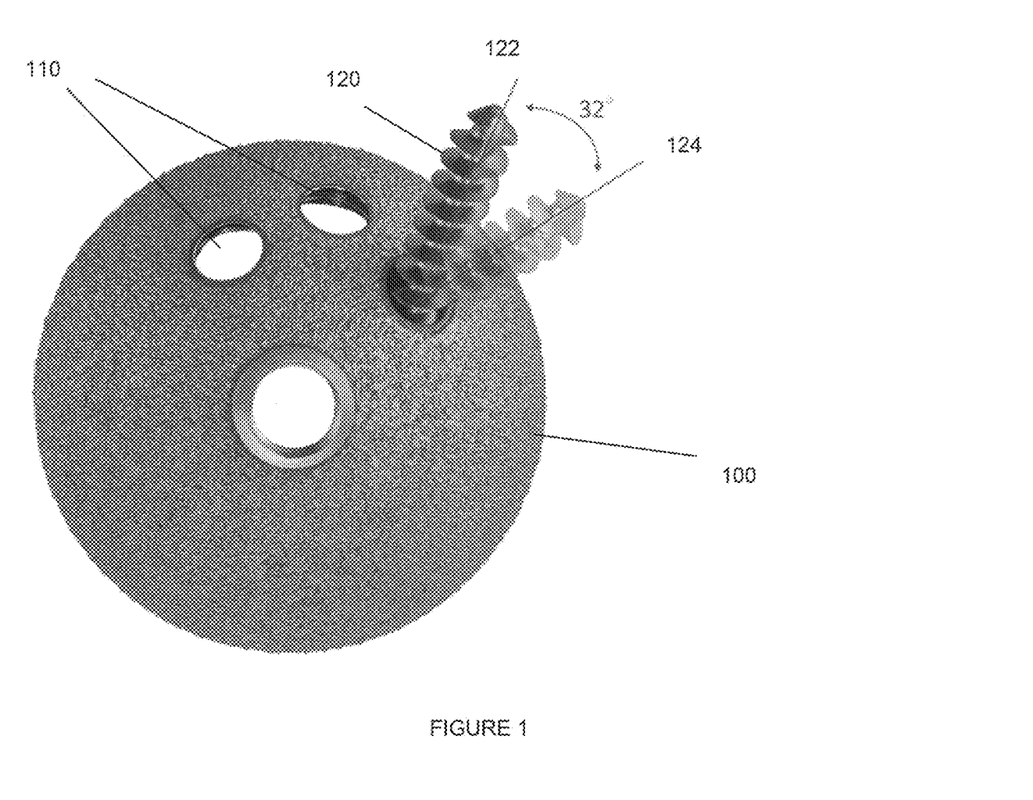
FIG. 1 is a perspective illustration of an implant device showing two screw placement vectors for one of a plurality of possible screw placement locations.

As set forth in the background section earlier in this document, orthopaedic implant apparatus or devices, referred to herein as an implant, or implants, are usually fixed to adjacent bone using screws. FIG. 1 shows a view of an example of an implant comprising an acetabular cup 100, which is adapted to be fixed to the pelvis of a patient receiving the implant 100. The implant 100 has a number of apertures 110, each of which is adapted to receive a fixation device, namely a screw 120. The apertures 110 represent a constraint that defines the implant entry locations at which screws 120 can be placed in use to fix the implant to the adjacent bone. Not all locations may be used. Although the screw entry location is a given constraint, the vector i.e. that axial direction or path along which the screw is in use disposed in order to fix the implant to the bone, can vary. This is illustrated by way of example in FIG. 1, in which it can be seen that a screw may be disposed through an entry location aperture along a first vector 122, or an alternative vector 124. As described earlier in this document, the decision as to where each screw should be directed can be complex and can have a significant influence as to whether or not the implant is effective. The screw length, and thus the vector length can also vary dependent on the implant and/or the bone, along with other possible parameters as described further below.

Figure 2:
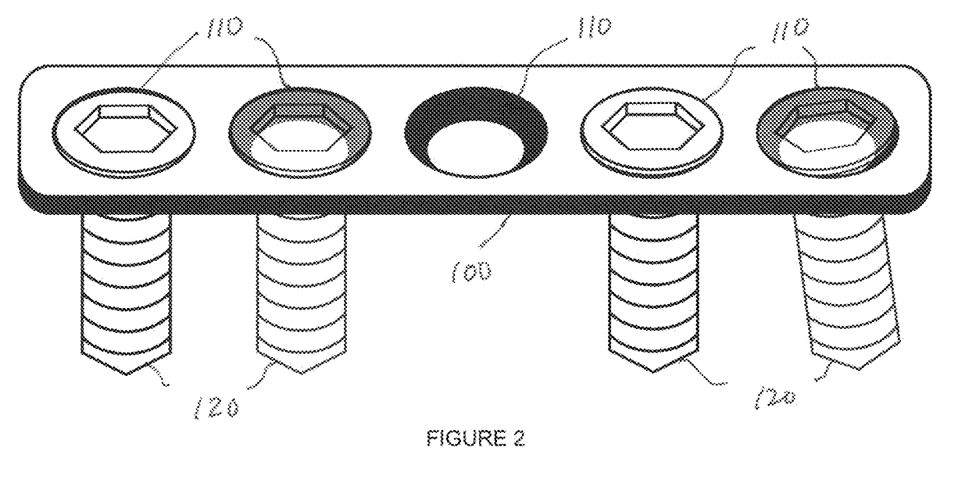
FIG. 2 is another example of an implant device.

In FIG. 2, a plate component 100 has multiple fixation locations, comprising screw holes 110 along its length for securing segments of a fractured long bone. Multiple screws 120 are used but not all holes require a screw for effective fixation. One possible fixation is shown by the 2 solid-line screws while an alternative fixation is shown by the transparent-line screws. The optimal fixation should depend on the bone quality under each hole and the underlying bone geometry.

Choosing a screw location, or a permutation of locations from a set of possible locations is an aspect of the invention.

In some implants, like the acetabular cup in the FIG. 1 example, there are a finite number of screw holes. In this scenario, given a set of possible locations (holes), placing a screw in one may preclude the placement of screws in other locations (e.g. due to proximity to the placed screw or screw path(s) intersecting with the path of the placed screw). The invention will calculate any preclusions and factor them into the generation of possible location permutations and their scoring and ranking, as described further below.

In another scenario, for custom 3D printed implants, the location and number of screws may be arbitrary depending on patient anatomy. The locations and number of screws is chosen to ensure sufficient fixation strength. In this case, the surgeon may proscribe a fixed number of screws he/she wishes to use and leave it to the invention to position and orient them. Or, the invention may be used to automatically find the optimal number of screws given surgical, anatomical, and/or manufacturing constraints.

Figure 3:
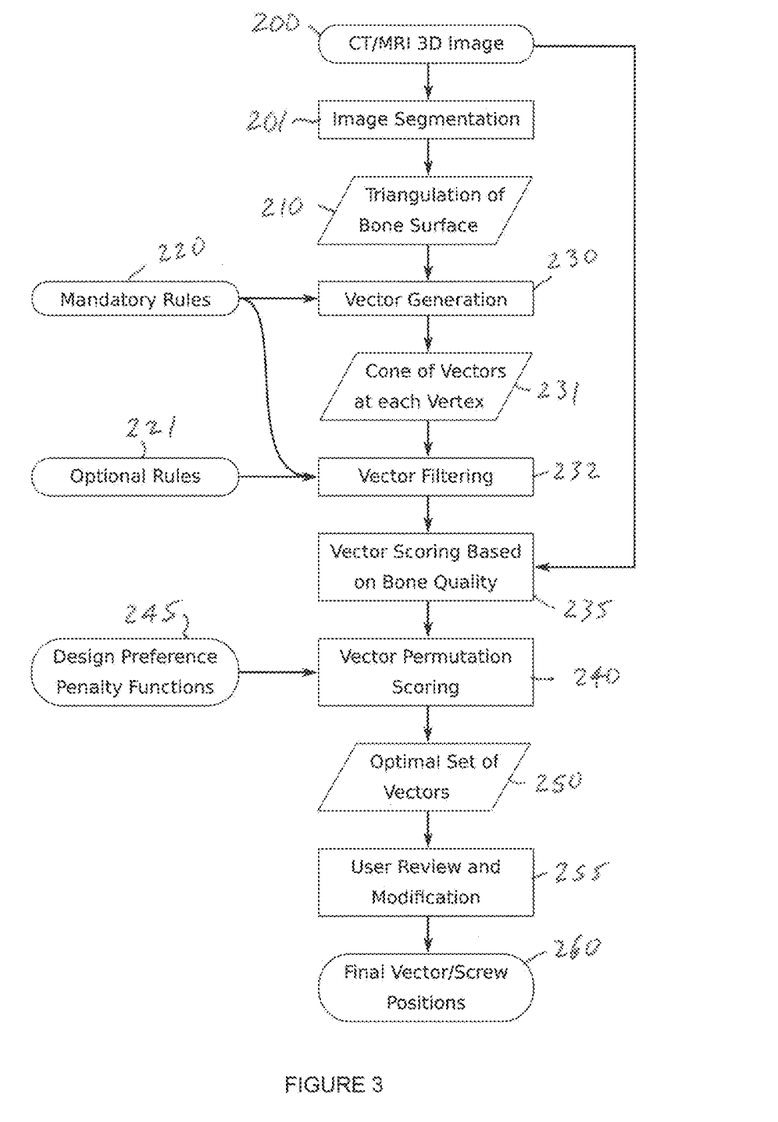
FIG. 3 is a flow chart showing a process according to one example of the invention.

FIG. 3 shows an example of a flow chart illustrating an overview of a process that may be performed according to the invention in order to assist the surgeon to decide on effective screw placement. The process of FIG. 3 will be described together with the apparatus shown diagrammatically in FIG. 4. It will be understood that the processes described with reference to FIGS. 3 and 4 may be carried out, at least in part, by a processor configured or programmed to execute instructions stored in memory.

The process begins at step 200 in which an input image is received for processing. The input image is a 3-D medical image of the bone or bones to receive the implant i.e. the bone or bones to which the implant is to be affixed. The image may be received as a file 305, and may be received over a network, and possibly directly from an imaging apparatus 300. The image should have voxel values related to the density of the bone they represent. For example, the image may comprise regular or quantitative X-ray computed tomography (CT), or magnetic resonance images (MRI) taken with a bone-density-resolving sequence, as demonstrated for example in https://www.ncbi.nlm.nih.gov/pubmed/10602850. If the image comprises regular clinical CT or MRI, then the density of the bone in one region relative to another can be determined. If the image comprises quantitative CT or MRI, then an absolute bone density can be calculated. Therefore the process can use both modalities. It will be apparent that other imaging processes or data can be provided, as long as the data is sufficient to enable at least a relative bone density to be determined. Moreover, the image data may be provided in a pre-processed form i.e. the processing required to achieve the required input bone density model may be performed as part of a separate process and/or using a separate machine.

Processor of server computer 310 (FIG. 4) performs the processing required in the subsequent steps described below. It will be understood that the processing can be performed using one or more machines at one or more locations. The input bone image from step 200 is processed in steps 201 and 210 to provide an input bone model. In one example the input bone model is a triangulated surface model of the bone. This may be performed using image segmentation software. The model is decimated or oversampled to achieve triangle edge lengths of approximately 1 mm, or as appropriate for the implant and implant fixation. For example, an implant using very small screws that can be placed closer together will required a smaller triangulation edge length to produce a higher resolution surface mesh. A surface normal may be calculated at each vertex. As described above, the model includes at least relative bone density data. An image representative of the input bone model is shown in FIG. 5. In this example the bone comprises a pelvic bone.

Input rules are provided in steps 220 and 221. These may be provided at any earlier step in the process if required. The rules may be conveniently separated into those which must be followed because they relate to constraints that are fixed, for example the geometry of the implant, and those that may be selected for other reasons. The rules for the fixed constraints may be described as mandatory rules, and may include the following as examples:

- The proscribed position and orientation of any implant components to be fixed. How these components must be placed will constraint where screws can be placed and/or orientated. For example, an acetabular cup component is often required to be fixed at surgeon-proscribed anatomical angles (anteversion and abduction) and position to restore patient function. These requirements constraint the position of the screw holes in the cup but not necessarily the angle at which screws much be inserted through the holes.
- The total number of screws or the maximum/minimum number of screws
- Allowable entry and exit regions (i.e. locations) for sets of screws, or for each screw either on the implant or on the patient bone surface. These locations may either be discrete (e.g. pre-drilled holes on a plate) or any point within a continuous region, e.g. the ilium of the pelvis. Regions to avoid may include regions with predetermined bone loss, bone tumour, necrosis, or other abnormalities.
- The minimum distance of screws to adjacent bones during joint movement Additional rules can be added dependent on further optional constraints that can be defined by the surgeon for example. These rules may be considered as optional rules, and can include, for example:

- Minimum angle of entry into bone
- Angular and positional constraints depending on the type of implant and the surgical approach that the surgeon wishes to adopt. The surgical approach defines the region of the bone the surgeon has access to.
- Angular constraints imposed by the interaction between interfacing implant components. Screws inserted into one component at certain angles any impede another component being attached or functioning with the first component.
- In the case of patient-specific implants, angular and positional constraints depending on the manufacturing process
- The maximum/minimum angle of entry of screws into bone
- The maximum/minimum cortical bone thickness at points of screw entry or exit
- The maximum/minimum bone density at points of screw entry or exit
- Any positional and orientation constraints imposed by surgical guidance systems, from mechanical cutting guides to digital navigation systems and robotic surgery systems.

The rules, and the rule structure, listed above is one example. It will be understood that the rules may be changed as required, and that the overall process may be performed again, or iteratively, with different rules or changes to the rules, as required. Moreover, the screw placement vectors that result from the process may be compared with changes made to the rules, so that a surgeon may compare the use of different models or types of implant, or different surgical approaches. The information may be used to explore the viability of the type of procedure and/or the type of implant for the given bone.

Rules (e.g. maximum vector angle to bone surface) and rule parameters (e.g. 60 degrees) may be also be automatically derived through machine-learning. For a particular type of implant, given a training set of such implants with known fixation placements and bone morphology, e.g. from historical cases, a machine-learning algorithm could be used to automatically determine the optimal set of rules and rule parameters. These optimal rules would produce a fixation plan in a new bone that mimics how the implant was fixated in the training set examples.

One example of a suitable machine learning method is a genetic algorithm. In this implementation, the "genetic code" consists of a list of rules and their parameters. In each generation, there may be a number of genetic codes (initially randomly generated). In the mutation stage of the algorithm, rules may be randomly added to or removed from the genetic codes, and the parameters randomly perturbed. Alternatively, rules and parameters may be copied from one genetic code to another. Fixation vectors are then generated for each example in the training set using the rules in each of the genetic codes. The errors between the generated and actual fixation vectors are calculated and a subset of the genetic codes that generated fixation plans with the lowest error across the training set are passed onto the next generation. The algorithm iterates through generations until either a maximum number of generations is reached, an error threshold is reached, or the genetic codes have converged as defined by having less than a maximum amount of difference between each other over the last predefined number of generations.

In steps 230 and 231 a finite set of possible screw placement vectors is generated. Each vector starts at a point on the input bone model. This point is typically a vertex. As described above the vector defines the direction of the screw trajectory.

In one example, each rule is implemented programmatically as a filter function that takes as input a list of screw placement vectors and outputs a binary array that denotes whether each vector in the input list of vectors satisfies the rule.

A "cone" or hemisphere of vectors is generated at each vertex, with the vectors extending in all directions between parallel to the bone surface to directly normal to the bone surface. In the absence of the rules, this results in an infinite set. Filtering this initial set of vectors to remove those vectors that do not satisfy the rules results in a finite set of vectors. Filtering occurs in step 232.

To generate the finite set of vectors, the rules are applied in a selected order. For computational efficiency, we apply the most computationally efficient filters first to reduce the number of vectors that have to be filtered by less efficient filters. In one example, one or more of the mandatory rules referred to above are initially applied, and the magnitude of the resultant set of vectors is then determined. If the set is too large, then further rules are progressively applied. For example, as a first step, vectors may be passed through the allowable exit region filter to remove vectors that exit the bone model outside of allowable exit regions. Then the vectors are passed through each of the other optional rule filters to arrive at a set of filtered placement vectors.

Figures 5A, 5C:
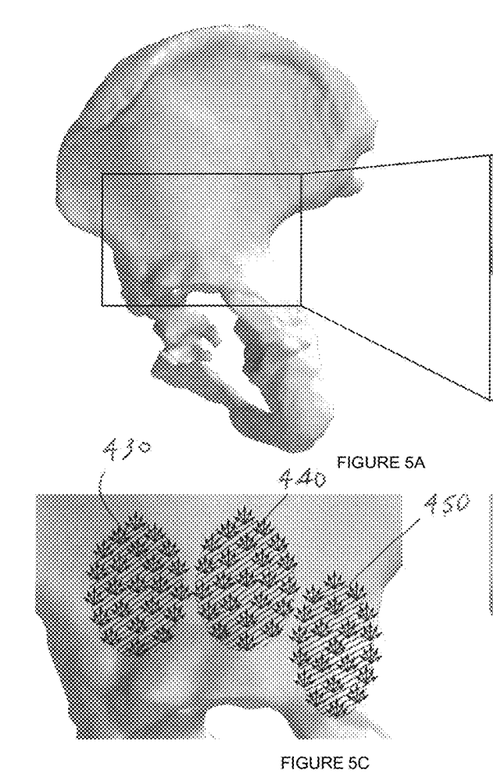
FIGS. 5A-F are illustrations showing a bone model and derivation of vector sets.
Figure 5B:
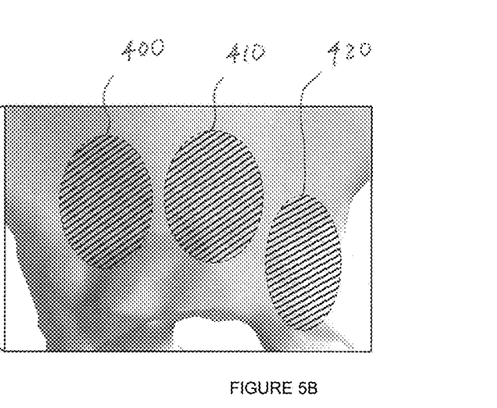
Figure 5D:
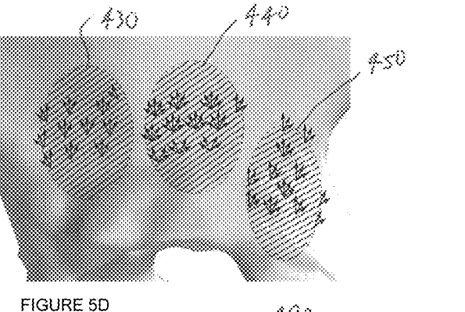

An example of the effect of applying the rules can be visualised with reference to FIG. 5B to 5F. In this example, three screws are to be placed in the ilium of the hemipelvis (FIG. 5A). In FIG. 5B, screw region rules (i.e. the constraint relating to the allowable location of each screw as imposed by the design and geometry of the implant) have been applied to produce 400, 410 and 420. Thus the theoretically infinite set of 3-vector combinations relating to the bone model of FIG. 5A has been filtered to a finite set of approximate magnitude $1 \times 10^{17}$, and the vector locations are shown graphically in the three regions 430 to 450 in FIG. 5C. For clarification, this refers to the number of possible permutations of k screws, not just the number of individual screw positions.

The next rules that are applied in this example are those relating to screw angle and spacing. Applying these rules further limits the possible vector combinations to a set having a magnitude of approximately $1 \times 10^6$ to $1 \times 10^8$. The set of vectors is now illustrated by the remaining arrows in FIG. 4D. At this stage, there may be a few hundred possible placement vectors per screw. Assuming an implant requiring three screws each with 200 vectors, this presents $1.6 \times 10^9$ combinations.

Rules may continue to be applied to the vector set in this manner until a vector set of a required magnitude has been determined for purposes of further processing. The required magnitude may vary depending on the implant or the procedure or both. The required magnitude may also be dependent on the processing resource which is available. A very large vector set might take an impractical time period to process.

Having generated a vector set of a desired or required magnitude, a further process can be used to select best or optimal screw placement. This finds an optimised combination within the vector set which occurs in step 240 of FIG. 2, and an example of a process is now described in more detail below.

Firstly, in step 235, the bone density information from the bone input model is used to determine, for example by calculation, an indication of the bone quality along each vector in the set. This can be achieved in different ways, and in one example, the bone density is summed along the length of the vector, which represents the axial length of the screw thread which would penetrate the bone. As mentioned above, an absolute value of bone density may not be necessary, as relative bone density may be sufficient for the purposes of comparing the results for the different vectors. Alternatively, finite-element analysis (FEA) can be used to predict peak bone strain around screws placed at proposed vectors as another measure of bone quality. Higher peak strain would indicated weaker bone and thus a lower score. In one example a bone quality score is calculated for each vector. The score is the sum of voxel values along the vector that have a voxel value within that of bone.

The vectors for each screw location are ranked according to the bone quality score for each vector as determined in the preceding step.

Figure 5E:
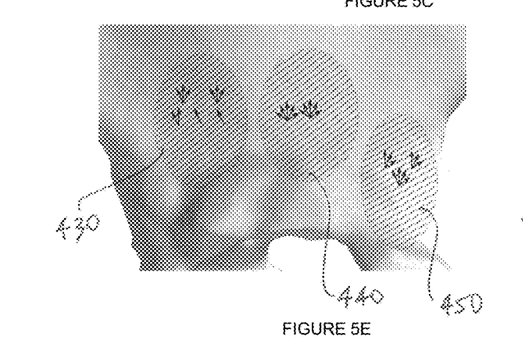
Figure 5F:
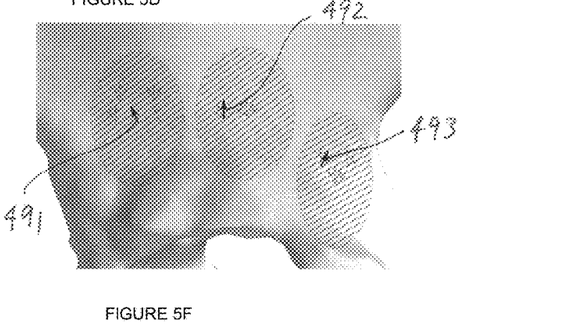

The top k vectors of the bone score rankings are selected for each screw location (FIG. 5E).

The results are used to generate all permutations of the k vectors per screw for n screws i.e. permutations for the k vectors across the various screw locations. For example, for k=2, n=2, there is the set of vector permutations v={[v11, v21], [v12, v21], [v11, v22], [v12, v22]} where the 1st subscript is the screw number and the 2nd subscript is the vector rank.

In step 240 we iterate through each permutation and compute a score. This step involves applying factors that relate to the particular permutation. This permutation score is compute as a weighted sum of "penalty" or "cost" functions 245 that represent soft constraints or design preferences on the placement of screws:

$$s(v)=b(v)+w1*f1(v)+w2*f2(v)+ \ldots +wn*fn(v)$$

B(v) is the inverse of the sum of each vectors bone quality score. f1 . . . n are the penalty functions each weighted by a corresponding scalar value w1 . . . n that controls the importance of the penalty function or design preference. Finding a permutation v with the smallest s results in the set of vectors (and therefore screws) that balances adherence to design preferences with bone quality around each screw, in addition to obeying the input design rules.

An example of a penalty function is one that calculates the variance in distance of each vector from a fixed point. Minimising this penalty function results in vectors equidistance from, for example, an anatomical landmark or a joint centre. Another penalty function may calculate the mean angle between each vector. Minimising this penalty function results in well-aligned screws that may simplify manufacturing or fixation during surgery. Alternatively, minimising the inverse of this penalty function results in screws fixing the implant to bone at different angles which will improve the strength and stability of the fixation. More than one penalty function can be used at once to account for multiple design preferences. The weighting of each function can vary depending on the implant or procedure.

Design preferences that may be implemented as penalty functions include:
  Separation between each screw and its nearest neighbour
  The amount of spread of all screws, e.g. variance in distance and direction from a fixed point.
  The concentration or spread of screws over general or specific anatomical regions
  The concentration or spread of screw over different parts of an implant component
  Screw distance to an anatomical landmark including anatomical points, lines, or regions
  Screw distance to external landmarks including those on the implant, another implant, or surgical guide
  Screw orientation to each other
  Screw orientation relative to anatomical axes
  Screw orientation relative to external axes including those on the implant, another implant, or surgical guide
  Number of screws placed in total
  Number of screws placed in specific regions defined either on the implant or on bone
  The position and orientation of implant components in order to optimise their function. For example, an acetabular cup to be fixed using screws may have a desired positioning that optimally restores patient function. However, at this position there may not be any valid screw paths. Therefore, a penalty functions allows us to find an optimal positioning with valid screw paths close to the desired position.
  Any preferences defined by surgical guidance systems, from mechanical cutting guides to digital navigation systems and robotic surgery systems.

Figure 4:
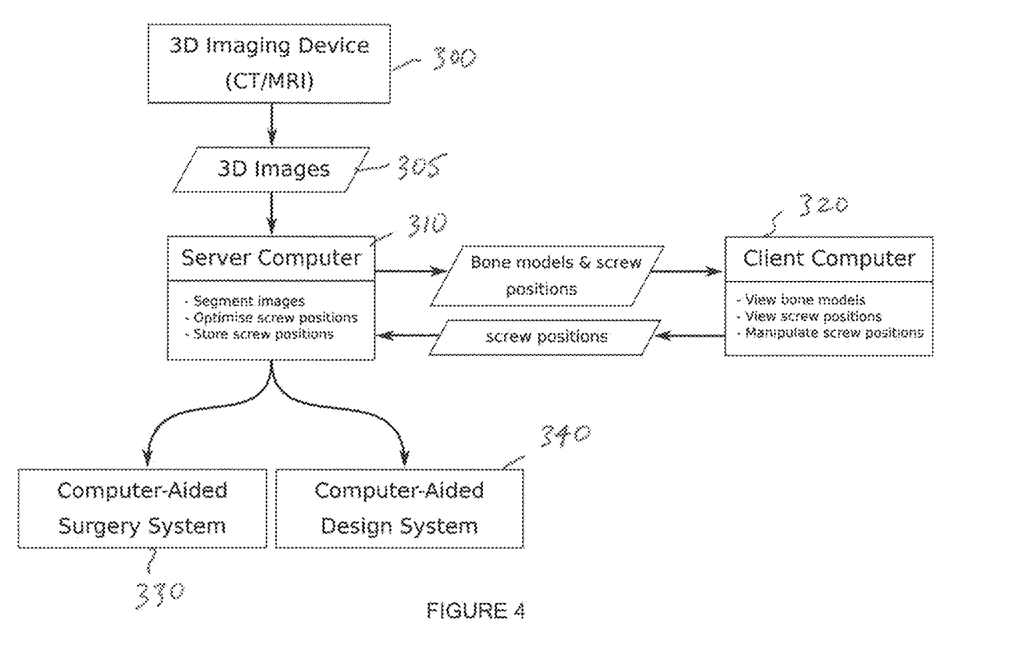
FIG. 4 is a diagram showing apparatus according to one possible example of the invention.

The computation that takes place for step 240 may in practice be is parallelised across multiple computing devices 310 (e.g. processors on CPU or GPU) because each permutation's score can be computed independently. Due to the potentially large number of permutations (e.g. k=10, n=5 gives 30,240 permutations), this parallelisation greatly reduces computing time.

In step 250, the permutation with the best (in this example the lowest) score from the process of step 240 is selected. Of course other methods of arriving at a score can be used. In other methods the score might instead be a higher score to denote a more favourable permutation. The selected permutation may be shown graphically, as for example screws 491 to 493 in FIG. 5E.

Figure 6:
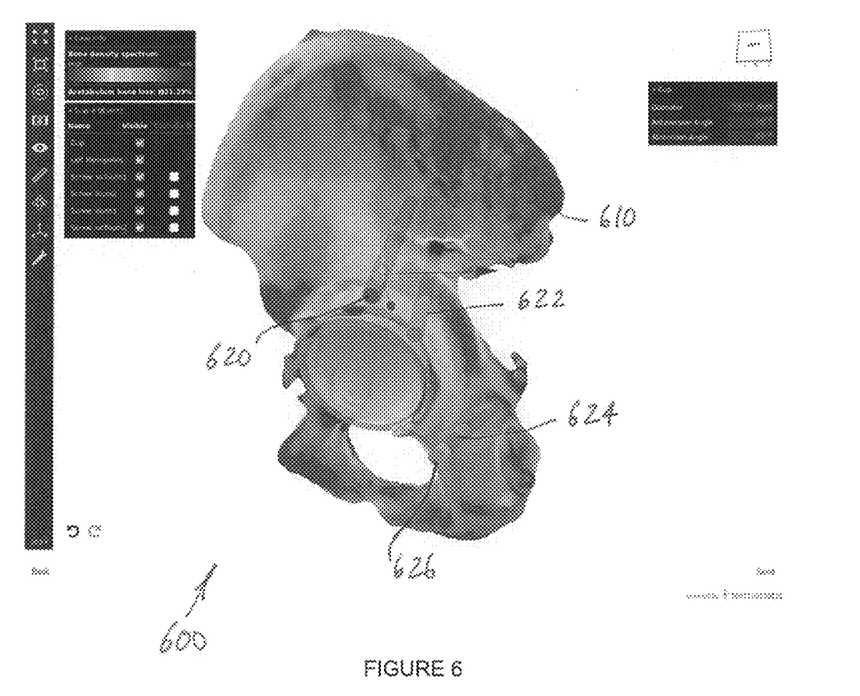
FIG. 6 is a screen shot showing a graphical user interface.

The result can also be provided in a clear graphical form for use by a surgeon to provide all information required to implement the optimised screw placement selection. This step occurs in output steps 255 and 260 of FIG. 3, and can be provided on an output machine and/or a visual display device 320 (FIG. 4). In a particular example, the selected screw placement is provided via a graphical user interface 600, as shown in FIG. 6. The automatically generated screw placements can be reviewed and manually adjusted via the user interface, which may be web based or cloud based. The interface displays 3D models of the bone 610, screws 620 to 626, and other relevant objects (e.g. other implant components) in an interactive scene. The user can click on the screws to select them, then translator or rotate them via click-and-drag actions or via widgets. The interface also includes controls for adding and removing screws. If a screw is moved or added, then the process described herein can be performed again to evaluate the change and if required compare it with the previous selection. Parameters that can be used for evaluating a selected placement permutation can be those described above, along with other measurements such as FEA-predicted bone strain around screws and/or FEA-predicted peak stress or strain in bone and implant.

The server computer 310 or client computer 320 may communicate with a computer-aided surgery system 330 and/or a computer-aided design system 340

From the foregoing it will be seen that systems and/or methods are provided which enables fast and reliable determination of desirable, or optimal, implant fixation device (e.g. screw) placement.

Unless the context clearly requires otherwise, throughout the description, the words "comprise", "comprising", and the like, are to be construed in an inclusive sense as opposed to an exclusive or exhaustive sense, that is to say, in the sense of "including, but not limited to".

Although this invention has been described by way of example and with reference to possible embodiments thereof, it is to be understood that modifications or improvements may be made thereto without departing from the scope of the invention. The invention may also be said broadly to consist in the parts, elements and features referred to or indicated in the specification of the application, individually or collectively, in any or all combinations of two or more of said parts, elements or features. Furthermore, where reference has been made to specific components or integers of the invention having known equivalents, then such equivalents are herein incorporated as if individually set forth.

Any discussion of the prior art throughout the specification should in no way be considered as an admission that such prior art is widely known or forms part of common general knowledge in the field.

What is claimed is:

1. A method for determining placement of a fixation apparatus for fixing an orthopaedic implant to bone, the method comprising:
   selecting a plurality of fixation locations;
   using a bone density model to determine a bone density associated with each fixation location;
   selecting a plurality of vectors for each fixation location;
   ranking the vectors according to the bone density associated with each fixation location; and
   selecting a combination or permutation of the fixation locations dependent on the ranking.

2. The method of claim 1 further comprising determining a selection of vectors with a highest bone density ranking for each fixation location.

3. The method of claim 2 further comprising generating permutations of the ranked vectors and locations.

4. The method of claim 3 further comprising determining a further ranking or score for each permutation.

5. The method of claim 4 further comprising selecting a permutation with the most favorable further ranking or score.

6. The method of claim 1 further comprising using the selected combination or permutation of the fixation locations to fix the implant to the bone.

7. A method for determining placement of a fixation apparatus for fixing an orthopaedic implant to bone, the method comprising:
   selecting a plurality of fixation vectors;
   using a bone density model to determine bone density associated with each vector along a length of the vector; and
   selecting at least one of the fixation vectors dependent on the determined bone density.

8. The method of claim 7 further comprising determining the density along the vector by summing or integrating bone density along the length of the vector.

9. The method of claim 7 further comprising extending or reducing the length of the vector dependent on the determined bone density.

10. The method of claim 7 further comprising selecting a fixation location for the fixation vectors.

11. The method of claim 10 further comprising using a bone density associated with a fixation location to determine whether to select the fixation location.

12. The method of claim 11 further comprising selecting a plurality of locations, and selecting a plurality of vectors for each location.

13. The method of claim 7 further comprising ranking vectors according to the bone density associated with each vector, and determining a selection of vectors with a highest bone density ranking for each of a plurality of fixation locations.

14. The method of claim 13 further comprising generating permutations of the ranked vectors and locations, determining a score for each permutation, and selecting a permutation with the most favorable ranking.

15. The method of claim 14 wherein the score may be dependent on one or more of:
   Relative vector proximity; and
   Relative vector alignment.

16. The method of claim 7 further comprising using the fixation vector to fix the implant to the bone.

17. A surgical implant fixation system comprising:
   at least one memory for saving instructions, and
   a processor configured to execute the instructions to:
      select a plurality of fixation locations at which to fix an implant to a bone,
      select a plurality of fixation vectors for each fixation location,
      determine permutations of fixation vectors across the selected fixation locations,
      determine a score for each permutation, and
      select a permutation with the best score.

18. The system of claim 17, wherein the processor uses machine learning to execute one or more steps therein.

19. The system of claim 17, wherein the processor is further configured to rank vectors according to a bone density associated with each vector.

20. The system of claim 19, wherein the processor is further configured to determine the bone density along the vector by summing or integrating bone density along a length of the vector.

21. The system of claim 20, wherein the processor is further configured to extend or reduce the length of the vector dependent on the determined bone density.

* * * * *